United States Patent
Le (10) Patent No.: US 10,174,283 B2
(45) Date of Patent: Jan. 8, 2019

(54) METHOD FOR CLEANING WATER DISPENSERS VIA USE OF SELECTIVELY BRED AND CULTIVATED GENERATIONS OF MICROBES

(71) Applicant: Khanh Le, San Jose, CA (US)

(72) Inventor: Khanh Le, San Jose, CA (US)

(73) Assignee: Cisbay Global Inc., San Jose, CA (US)

( * ) Notice: Subject to any disclaimer, the term of this patent is extended or adjusted under 35 U.S.C. 154(b) by 34 days.

(21) Appl. No.: 15/405,255

(22) Filed: Jan. 12, 2017

(65) Prior Publication Data

US 2018/0194653 A1 Jul. 12, 2018

(51) Int. Cl.
*C02F 3/00* (2006.01)
*C12N 1/22* (2006.01)
*C02F 3/34* (2006.01)

(52) U.S. Cl.
CPC .......... *C12N 1/22* (2013.01); *C02F 3/341* (2013.01); *C02F 3/348* (2013.01); *C02F 2305/06* (2013.01)

(58) Field of Classification Search
USPC .................. 210/601, 610, 611, 747, 909
See application file for complete search history.

(56) References Cited

U.S. PATENT DOCUMENTS

| | | | |
|---|---|---|---|
| 3,719,327 A | 3/1973 | McMahan | |
| 5,057,221 A * | 10/1991 | Bryant | C02F 3/06 210/610 |
| 5,494,580 A * | 2/1996 | Baskys | A62D 3/02 210/611 |
| 5,888,395 A * | 3/1999 | Carman | B09C 1/002 210/606 |
| 6,471,741 B1 | 10/2002 | Reinbergen | |
| 2005/0287283 A1 | 12/2005 | Dicks | |
| 2008/0213865 A1 | 9/2008 | Lai | |
| 2011/0281725 A1 | 11/2011 | Pullen | |
| 2013/0126427 A1 * | 5/2013 | Jones | C02F 3/006 210/615 |
| 2013/0183732 A1 * | 7/2013 | Mancinelli | C12N 1/14 435/162 |
| 2013/0264281 A1 * | 10/2013 | Miklos | C02F 3/006 210/605 |
| 2014/0234524 A1 | 8/2014 | Parks | |
| 2014/0342437 A1 * | 11/2014 | Carpenter | C12N 1/20 435/252.4 |

OTHER PUBLICATIONS

Hibbing et al. (Bacterial competition—surviving and thriving in the microbial jungle, Nat. Rev Microbiol., 8(1), pp. 15-25, Jan. 2010). (Year: 2010).*

* cited by examiner

Primary Examiner — Hayden Brewster (74) *Attorney, Agent, or Firm* — Tran & Associates (57) ABSTRACT

Systems and methods for cleaning a water dispenser by preparing a bioremediation solution with microbes, a growth medium, and water; injecting the bioremediation solution into a water supply; and flushing the water supply with the bioremediation solution.

16 Claims, 6 Drawing Sheets

FIG. 1

| |
|---|
| 1. Nutrients - Fermentation Media |
|     a. Carbon #1 source Dextrose or Glucose |
|     b. Carbon #2 source Sucrose |
| 2. Nitrogen – soy protein – Non-GMO |
| 3. Micronutrients – Calcium, Magnesium and Zinc |
| 4. Media is prepared using water supply and sterilized using stream sterilizer at 120 degrees Celsius for 45 minutes based on tank volume. |
| 5. Produce microbial products. At each stage QC methods are applied using standard plate count method for Shigella, E. Coli, Salmonella Yersinia and Psuedomonas beroginosa for their absence. All products are manufactured according to USEPA (United States Environmental Protection Agency) standards. |

METHOD FOR CLEANING WATER DISPENSERS VIA USE OF SELECTIVELY BRED AND CULTIVATED GENERATIONS OF MICROBES

This application is related to application Ser. No. 15/404,208 entitled "SYSTEMS AND METHODS FOR WATER REMEDIATION" and Ser. No. 15/405,247 entitled "ANIMAL FEED STOCK USING MICROBIAL ENHANCEMENTS", all of which are filed concurrently herewith, and the contents of which are incorporated-by-reference.

BACKGROUND

The present invention relates to cleaning of water dispensers such as drip lines or irrigation systems.

For aquatic applications, algae blooms are one of the most common problems encountered by lake and pond owners. More than just aesthetically unappealing, certain forms of algae may harbor potentially toxic bacteria. Conventional ways of solving algae blooms are expensive and/or environmentally harmful as follows:

Mechanical intervention—Mechanical methods of algae control include removing blooms with a rake, seine, screen or other tool. While useful for quickly remediating harmful or invasive growths, mechanical controls do not address the underlying conditions that caused the problem. To address the underlying conditions, they must be used in conjunction with other methods.

Physical intervention—Some lakes and ponds are more prone to algae growth than others—factors such as aeration, light and nutrient content all affect whether or not algae will bloom. Adding an aerator or making other changes that promote these positive physical characteristics is one method of preventing algae outbreaks.

Biological intervention—Ponds and lakes are complex ecosystems. Under ideal conditions, they will attain a balance in which invasive algae growth is kept to a minimum. By introducing certain fish or insects into this ecosystem, we can help it attain a state of equilibrium that minimizes algae blooms naturally.

Material intervention—One of the most common methods utilized for controlling noxious algal blooms is with the use of algaecides. When utilized by a professional, algaecides can provide safe and effective management of harmful algae blooms. Out of balance populations of algae can be quickly brought under control when applications are conducted in a timely manner and under appropriate environmental conditions. Fish populations can benefit as well from improved spawning habitat and increased access to forage.

SUMMARY

In one aspect, a method for cleaning a water dispenser includes preparing a bioremediation solution with microbes, a growth medium, and water; injecting the bioremediation solution into a water supply; and flushing the water supply with the bioremediation solution.

In another aspect, a watering system includes a container for a bioremediation solution with microbes, a growth medium, and water; a pump for injecting the bioremediation solution into a water supply; and a water dispenser coupled to the pump, wherein the pump flushes the water supply with the bioremediation solution to clear the water dispenser.

In another aspect, a method for water remediation includes preparing a microbial solution with microbes, a growth medium, and water; iteratively and selectively breeding generations of microbes to arrive at a predetermined microbial solution in a highly concentrated form of at least $1\times10^9$ cfu/ml (colony-forming units per milliliter); and dispensing the microbial solution into the water, wherein the microbes metabolizes excess nutrients and uses microbial desalination to reduce water salinity.

Implementations may include one or more of the following. A member of Bacillus can be the microbe. The growth medium can be a carbon source. The growth medium can be sugar, molasses, or maltodextrin. The solution can have 1 part microbes, 10 part carbon source, and 1000 parts water. The solution can use as a carrier one of: amino acid, maltodextrin, wheat, or corn. The microbe can be one of: Bacillus (B.) acidiceler, B. acidicola, B. acidiproducens, B. acidocaldarius, B. acidoterrestrisr, B. aeolius, B. aerius, B. aerophilus, B. agaradhaerens, B. agri, B. aidingensis, B. akibai, B. alcalophilus, B. algicola, B. alginolyticus, B. alkalidiazotrophicus, B. alkalinitrilicus, B. alkalisediminis, B. alkalitelluris, B. altitudinis, B. alveayuensis, B. alvei, B. amyloliquefaciens, B. a.* subsp. *amyloliquefaciens, B. a.* subsp. *plantarum, B. amylolyticus, B. andreesenii, B. aneurinilyticus, B. anthracia, B. aquimaris, B. arenosi, B. arseniciselenatis, B. arsenicus, B. aurantiacus, B. arvi, B. aryabhattai, B. asahii, B. atrophaeus, B. axarquiensis, B. azotofixans, B. azotoformans, B. badius, B. barbaricus, B. bataviensis, B. beijingensis, B. benzoevorans, B. beringensis, B. berkeleyi, B. beveridgei, B. bogoriensis, B. boronophilus, B. borstelensis, B. brevis Migula, B. butanolivorans, B. canaveralius, B. carboniphilus, B. cecembensis, B. cellulosilyticus, B. centrosporus, B. cereus, B. chagannorensis, B. chitinolyticus, B. chondroitinus, B. choshinensis, B. chungangensis, B. cibi, B. circulans, B. clarkii, B. clausii, B. coagulans, B. coahuilensis, B. cohnii, B. composti, B. curdlanolyticus, B. cycloheptanicus, B. cytotoxicus, B. daliensis, B. decisifrondis, B. decolorationis, B. deserti, B. dipsosauri, B. drentensis, B. edaphicus, B. ehimensis, B. eiseniae, B. enclensis, B. endophyticus, B. endoradicis, B. farraginis, B. fastidiosus, B. fengqiuensis, B. firmus, B. flexus, B. foraminis, B. fordii, B. formosus, B. fortis, B. fumarioli, B. funiculus, B. fusiformis, B. galactophilus, B. galactosidilyticus, B. galliciensis, B. gelatini, B. gibsonii, B. ginsengi, B. ginsengihumi, B. ginsengisoli, B. globisporus, B. g.* subsp. *globisporus, B. g.* subsp. *marinus, B. glucanolyticus, B. gordonae, B. gottheilii, B. graminis, B. halmapalus, B. haloalkaliphilus, B. halochares, B. halodenitrificans, B. halodurans, B. halophilus, B. halosaccharovorans, B. hemicellulosilyticus, B. hemicentroti, B. herbersteinensis, B. horikoshii, B. horneckiae, B. horti, B. huizhouensis, B. humi, B. hwajinpoensis, B. idriensis, B. indicus, B. infantis, B. infernus, B. insolitus, B. invictae, B. iranensis, B. isabeliae, B. isronensis, B. jeotgali, B. kaustophilus, B. kobensis, B. kochii, B. kokeshiiformis, B. koreensis, B. korlensis, B. kribbensis, B. krulwichiae, B. laevolacticus, B. larvae, B. laterosporus, B. lautus, B. lehensis, B. lentimorbus, B. lentus, B. licheniformis, B. ligniniphilus, B. litoralis, B. locisalis, B. luciferensis, B. luteolus, B. luteus, B. macauensis, B. macerans, B. macquariensis, B. macyae, B. malacitensis, B. mannanilyticus, B. marisflavi, B. marismortui, B. marmarensis, B. massiliensis, B. mesonae, B. methanolicus, B. methylotrophicus, B. migulanus, B. mojavensis, B. mucilaginosus, B. muralis, B. murimartini, B. mycoides, B. naganoensis, B. nanhaiensis, B. nanhaiisediminis, B. nealsonii, B. neidei, B. neizhouensis, B. niabensis, B. niacini, B. novalis, B. oceanisediminis, B. odysseyi, B. okhensis, B. okuhidensis, B. oleronius, B. oryzaecorticis, B. oshimensis, B. pabuli, B. pakistanensis, B. pallidus, B. pallidus, B. panacisoli, B. panaciterrae, B. pantothenticus, B. parabre-* vis, *B. paraflexus, B. pasteurii, B. patagoniensis, B. peoriae, B. persepolensis, B. persicus, B. pervagus, B. plakortidis, B. pocheonensis, B. polygoni, B. polymyxa, B. popilliae, B. pseudalcalophilus, B. pseudofirmus, B. pseudomycoides, B. psychrodurans, B. psychrophilus, B. psychrosaccharolyticus, B. psychrotolerans, B. pulvifaciens, B. pumilus, B. purgationiresistens, B. pycnus, B. qingdaonensis, B. qingshengii, B. reuszeri, B. rhizosphaerae, B. rigui, B. ruris, B. safensis, B. salarius, B. salexigens, B. saliphilus, B. schlegelii, B. sediminis, B. selenatarsenatis, B. selenitireducens, B. seohaeanensis, B. shacheensis, B. shackletonii, B. siamensis, B. silvestris, B. simplex, B. siralis, B. smithii, B. soli, B. solimangrovi, B. solisalsi, B. songklensis, B. sonorensis, B. sphaericus, B. sporothermodurans, B. stearothermophilus, B. stratosphericus, B. subterraneus, B. subtilis, B. s.* subsp. *inaquosorum, B. s.* subsp. *spizizenii, B. s.* subsp. *subtilis, B. taeanensis, B. tequilensis, B. thermantarcticus, B. thermoaerophilus, B. thermoamylovorans, B. thermocatenulatus, B. thermocloacae, B. thermocopriae, B. thermodenitrificans, B. thermoglucosidasius, B. thermolactis, B. thermoleovorans, B. thermophilus, B. thermoruber, B. thermosphaericus, B. thiaminolyticus, B. thioparans, B. thuringiensis, B. tianshenii, B. trypoxylicola, B. tusciae, B. validus, B. vallismortis, B. vedderi, B. velezensis, B. vietnamensis, B. vireti, B. vulcani, B. wakoensis, B. weihenstephanensis, B. xiamenensis, B. xiaoxiensis,* and *B. zhanjiangensis.*

Advantages of the above systems may include one or more of the following. The selectively bred bacteria form a bio-solution to help maintain ponds and lakes clean and clear the natural way. The microbes to break out the excess nutrients, pull them away from the water column and restate the water to its naturally beautiful and healthy condition without the undesirable side effects of chemicals.

BRIEF DESCRIPTION OF THE DRAWINGS

The novel features that are considered characteristic of the present invention are set forth with particularity in the appended claims. The invention itself, however, both as to its organization and its method of operation, together with additional objects and advantages thereof, will best be understood from the following description of specific embodiments when read in connection with the accompanying drawings, in which:

DESCRIPTION OF THE PREFERRED EMBODIMENTS

The following detailed description is of the best presently contemplated modes of carrying out the invention. This description is not to be taken in a limiting sense, but is made merely for the purpose of illustrating the general principles of the invention, since the scope of the invention best is defined by the appended claims.

Structural and operational characteristics attributed to forms of the invention at first described also shall be attributed to forms later described, unless such characteristics obviously are inapplicable, or unless specific exception is made.

A selectively bred microbial solution is disclosed with multiple single microbial series separately cultivated and followed with cross cultivation among those microbial series in a specific sequence and contains each of those microbial series, and by-products produced by those crossly cultivated microbial series are used for applications in modifying water quality. After the selective breeding through the fermentation, the selectively bred naturally-occurring microorganism is provided as a highly concentrated solution with the ability to digest excess nutrients to clear the water.

In a water enhancement embodiment, the selectively bred bacteria forms a bio-solution to help maintain ponds and lakes clean and clear the natural way. The microbes to break out the excess nutrients, pull them away from the water column and restate the water to its naturally beautiful and healthy condition without the undesirable side effects of chemicals.

Figure 1:
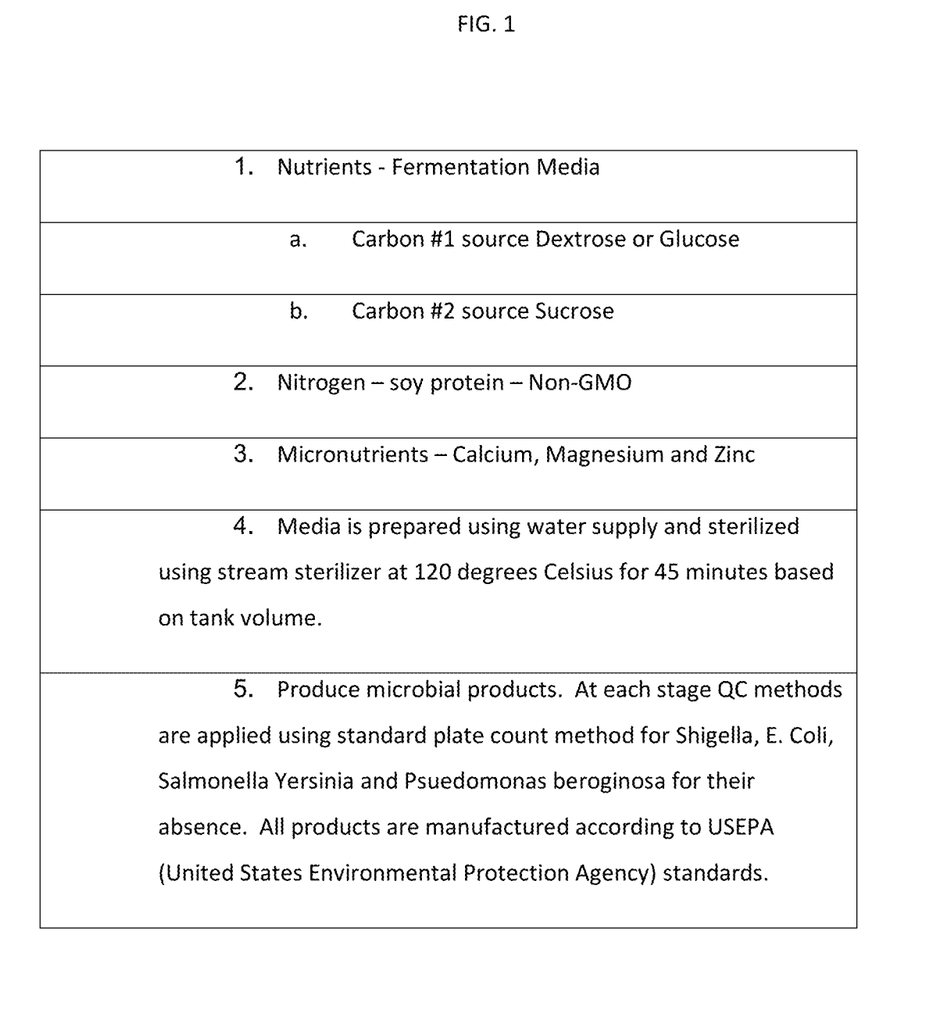
FIG. 1 shows an exemplary process to selectively breed the microbes for aquaculture or water use.

FIG. 1 shows an exemplary process to selectively breed the microbes for water use. First, fermentation media are prepared with a nutrient supply (1). The nutrients can include a carbon source Dextrose or Glucose. Additional carbon sources can be used with the dextrose or glucose singly or in combination. For example, another carbon source can be sucrose, for example. Next, a nitrogen source is provide such as soy protein that has not been genetically modified (2). Next, in (3), micronutrients—Calcium, Magnesium and Zinc are provided. A person of ordinary skilled in the art appreciates that various compositions of the fermentation media can be prepared so long as the nutrients, one or more of the carbon sources, and the micronutrients are included.

Figure 2A:
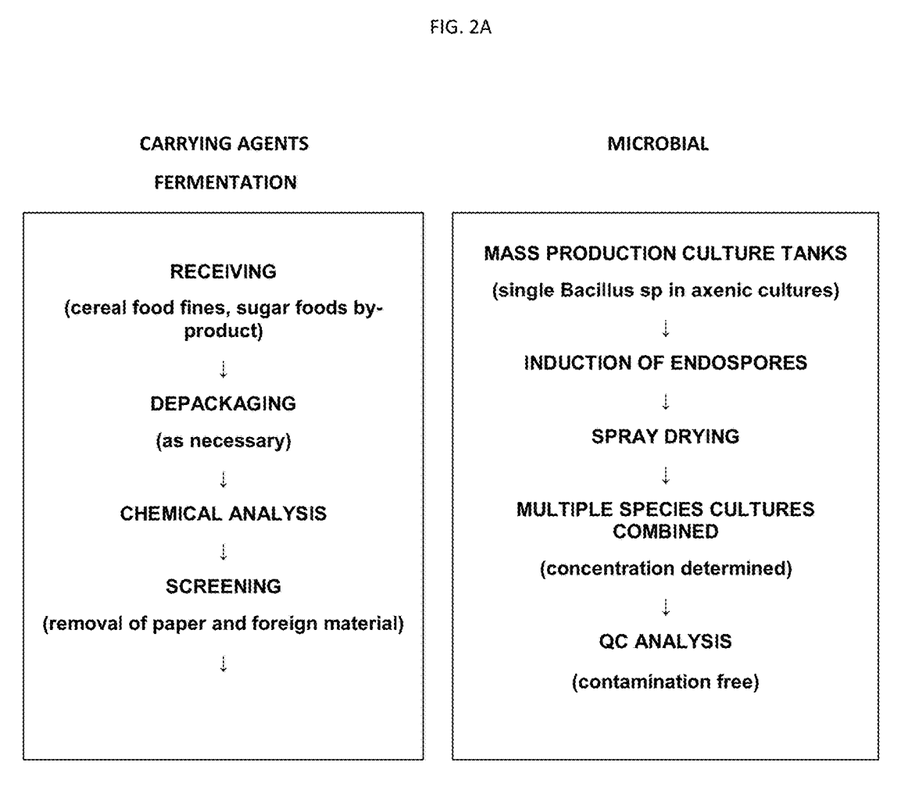
FIGS. 2A-2B show exemplary processes to produce microbial products.
Figure 2B:
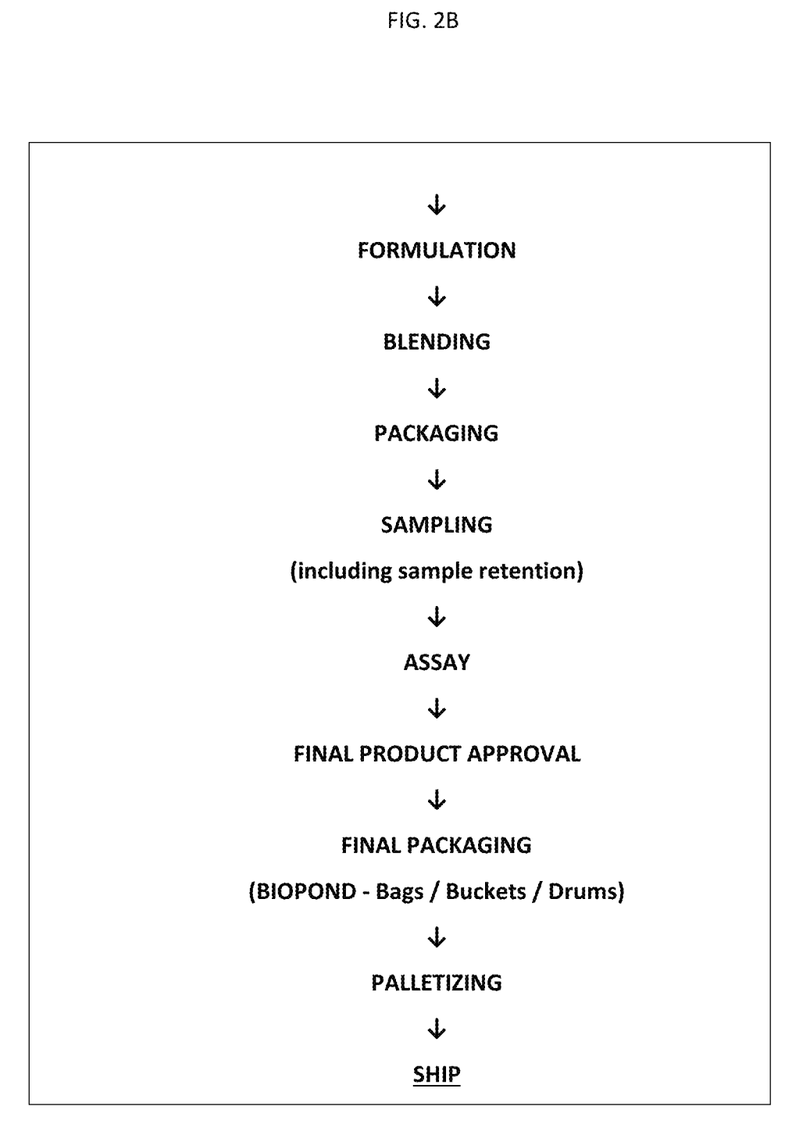

In (4), the fermentation media is prepared using water supply and sterilized using stream sterilizer at 120 degrees Celsius for 45 minutes, but the temperature and time can be varied in accordance with tank volume. In (5), the process produces the microbial products, as is detailed in FIG. 2. At each stage, quality control methods are applied using standard plate count method for *Shigella, E. Coli, Salmonella Yersinia* and *Psuedomonas beroginosa* for their absence. All products are manufactured according to USEPA (United States Environmental Protection Agency) standards.

The Microbial Strain selection and profile of microbial genes are carefully selected to form the formulation of products. Through strain selections, screening and improvement, the system generates various microbes for clearing water. For example, *Bacillus Subtilus* has 4,100 genes.

These genes each contain approximately 2000 traits. Each one of these traits and its mutation has over 1000 profiles and sub-profiles.

The biodiversity of *Bacillus* group and beneficial traits of bacillus species are useful in removing excess nutrients from the water column. *Bacillus* genus is widely spread in nature. *Bacillus* species such as *B. Subtilus, B. Amyloliquefaciens, B. lichniformis, Bacillus amyloliquefaciens, Bacillus lichniformis, Bacillus pumilus, Bacillus subtilis,* or *Pseudonomas putida* are carefully selected, for their specific profile which contains beneficial traits.

Figure 3A:
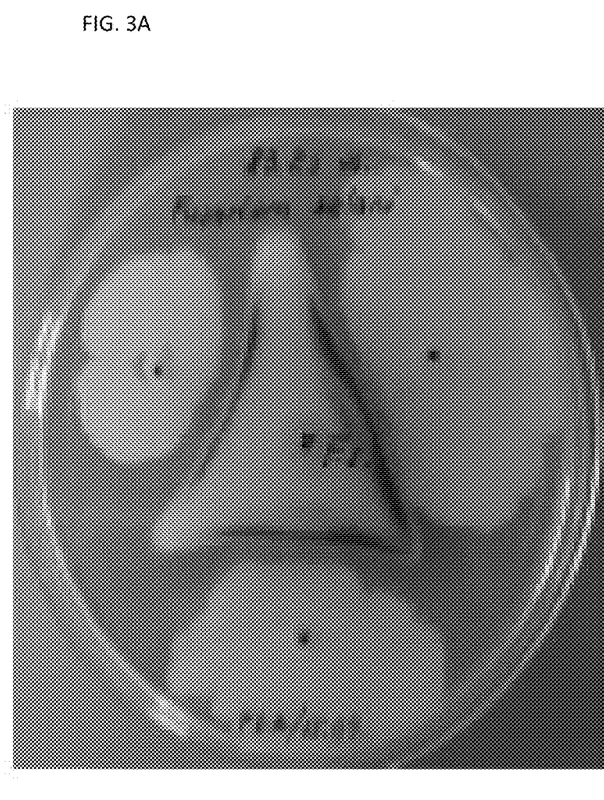
FIGS. 3A-3B show exemplary microbial activity expressed by different *Bacillus* spp. strains.
Figure 3B:
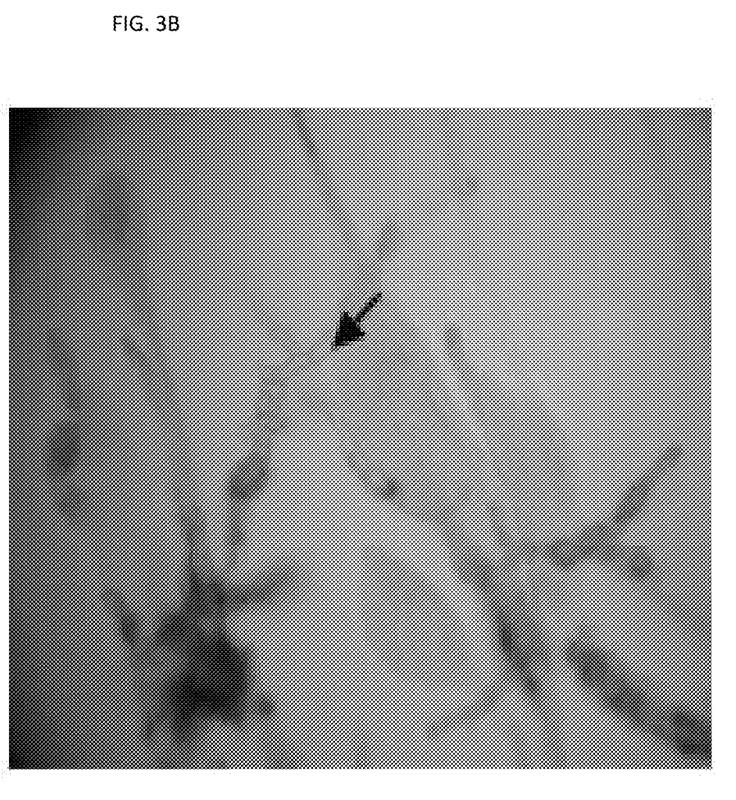

Each single microbial series is separately cultivated in its designated cultivation medium, and the optimal pH in the growing and reproduction of different microbial series also varies. Therefore, proper control and regulation of pH of the cultivation medium are provided in the course of bacterial cultivation and fermentation. The microbial series acquires energy through aerobic respiration. However, the aerobic respiration generally has to rely upon only the oxygen dissolved in the cultivation medium, i.e., the dissolved oxygen, and the containment of the dissolved oxygen in the cultivation medium is not always provided in sufficient amount and will be soonest consumed by bacteria since oxygen is difficult to get dissolved in water. Therefore, constant air supply to the microbial series is provided without interruption in the course of the cultivation and fermentation of the microbial series. Compositions of cultivation medium selected and the optimal growing environment conditions for each microbial series are detailed as follows:

FIG. 3A-3B shows exemplary microbial activity expressed by different *Bacillus* spp. Strains. FIG. 3A shows exemplary *Bacillus* spp. antagonistic activity against fusarium solani; while FIG. 3B shows exemplary fungal cell wall degradation, cell lysis and cytoplasm bleeding due to *Bacillus* spp. extracellular enzymes.

In a water cleaning embodiment called BIOPOND, the solution provides an all-natural, extremely concentrated beneficial microbes. When applied to water, the solution reduces ammonia, nitrate, nitrite and phosphorus. The solution binds phosphate, reduces water salinity, COD, and BOD. The solution removes toxic blue-green algae, hydrogen sulfide, and odors, reduces organic waste, bottom sludge and suspended solids, is safe for fish, pets, birds, livestock, plants and wildlife. The solution helps maintain optimum pH and create a balanced ecosystem and is highly effective biological filtration process of mineralization, nitrification and denitrification. Water is cleared naturally by removing excess nutrients from the pond. The BioPond application is simple and costs efficient solution available either by the biodegradable packets ready to toss or easy to incubate for industrial cost effective applications. The dosage is calculated based on the volume of water in acre-foot.

BIOPOND is a blend of naturally occurring beneficial aerobic and facultative anaerobic microbes that is effective in reducing water column nutrients in lakes, ponds, and organic wastewater. BioPond improves water quality without the undesirable side effects of chemical treatments. This is done as BioPond rapidly metabolizes excess nutrients and pulling them from the water column and uses microbial desalination cells to reduce water salinity.

The application of beneficial microbes is the key to a healthy water environment, effortless, all-natural, eco-friendly simple solution to manage ponds, lakes and wastewater treatment in a balanced ecosystem. Beneficial microbes are "good" bacteria, naturally occurring microorganisms that perform their work by producing enzymes and provide intelligent to detect the organics present to continue produce specifically those enzymes needed to break down the organics present. These microbes are capable of improving water quality and clarity by targeting organic particulates and excess nutrients, such as Nitrogen and Phosphorus, brought in by various sources.

Since they are naturally occurring and present in low concentrations, microbes in the ponds are not able to affect the water quality and clarity on their own. The BioPond application of concentrated beneficial microbes can exponentially boost their populations giving them the ability to affect water quality and clarity.

Any microbial spores and/or colonies can be preserved using methods and solutions of some embodiments. Spores and/or colonies of beneficial water and water pathogen biological control microorganisms are preferred. Microorganisms that grow rapidly and colonize substrata in water after treatment with compositions of the invention are particularly preferred. These include, but are not limited to bacteria, e.g., *Bacillus* species such as *Bacillus subtilis, Bacillus cereus, Bacillus penetrans, Bacillus licheniformis*; fungi, e.g., *Trichoderma species* such as *Trichoderma hamatum, Trichoderma harzianum, Trichoderma polysporum, Trichoderma konigii*, and *Trichoderma viride*; and yeast species such as *Saccharomyces cerevisiae*. As illustrated below, mixtures of microorganisms can also be preserved, and are preferred in many embodiments. Examples are given hereafter.

Water miscible dry powders and/or granules such as lyophilized preparations of spores and/or colonies are preferred in many embodiments. The amount of spores or microorganisms added to solutions of the invention is not fixed per se, and necessarily is dependent upon the degree of water remediation required, the number and identity of microorganism species needed in the formulation, and the concentration of other ingredients in the formulation. Typical embodiments contain sufficient spores and/or colonies to deliver from about 1000 to about 1,000,000 colony forming units (CFU) per square foot when the preparation is delivered.

The carrier for the microbes solution can be one of: maltodextrin, wheat, or corn. The resulting solution has a high concentration of microbes as detailed in the following examples. The colony-forming unit (CFU or cfu) is a measure of viable bacterial or fungal cells. CFU measures only viable cells. For convenience the results are given as CFU/mL (colony-forming units per milliliter) for liquids, and CFU/g (colony-forming units per gram) for solids.

EXAMPLE 1 (BIOPOND)

Microbes:
 *Bacillus amyloliquefaciens* at $0.91 \times 10^9$ cfu/g
 *Bacillus lichniformis* at $0.30 \times 10^9$ cfu/g
 *Bacillus pumilus* at $0.71 \times 10^9$ cfu/g
 *Bacillus subtilis* at $1.10 \times 10^9$ cfu/g
Carrier: Wheat

EXAMPLE 2 (BIOPOND)

Microbes:
 *Bacillus amyloliquefaciens* at $4.45 \times 10^9$ cfu/g
 *Bacillus lichniformis* at $1.48 \times 10^9$ cfu/g
 *Bacillus pumilus* at $3.35 \times 10^9$ cfu/g
 *Bacillus subtilis* at $4.75 \times 10^9$ cfu/g
 *Pseudonomas putida* at $2.45 \times 10^8$ cfu/g
Carrier: Corn Distiller and Dry Grain with Soluble

EXAMPLE 3 (BIOPOND)

Microbes:
 *Bacillus amyloliquefaciens* at $4.45 \times 10^9$ cfu/g
 *Bacillus lichniformis* at $1.48 \times 10^9$ cfu/g
 *Bacillus pumilus* at $3.35 \times 10^9$ cfu/g
 *Bacillus subtilis* at $4.75 \times 10^9$ cfu/g
 *Pseudonomas putida* at $2.45 \times 10^8$ cfu/g
Carrier: Maltodextrin and Amino Acid Complex

EXAMPLE 4 (BIOPOND)

Microbes:
    *Bacillus amyloliquefaciens* at $0.91 \times 10^9$ cfu/g
    *Bacillus lichniformis* at $0.30 \times 10^9$ cfu/g
    *Bacillus pumilus* at $0.71 \times 10^9$ cfu/g
    *Bacillus subtilis* at $1.10 \times 10^9$ cfu/g
Carrier: Wheat

EXAMPLE 5 (BIOPOND)

Microbes:
    *Bacillus amyloliquefaciens* at $1.30 \times 10^9$ cfu/g
    *Bacillus lichniformis* at $0.30 \times 10^9$ cfu/g
    *Bacillus pumilus* at $1.80 \times 10^9$ cfu/g
    *Bacillus subtilis* at $1.80 \times 10^9$ cfu/g
Carrier: Wheat

EXAMPLE 6 (BIOPOND)

Microbes:
    *Bacillus amyloliquefaciens* at $0.36 \times 10^9$ cfu/g
    *Bacillus lichniformis* at $0.71 \times 10^9$ cfu/g
    *Bacillus pumilus* at $0.50 \times 10^9$ cfu/g
    *Bacillus subtilis* at $0.50 \times 10^9$ cfu/g
Carrier: Distillers Dry Grain

EXAMPLE 7 (BIOPOND)

Microbes:
    *Bacillus amyloliquefaciens* at $4.45 \times 10^9$ cfu/g
    *Bacillus lichniformis* at $1.48 \times 10^9$ cfu/g
    *Bacillus pumilus* at $3.35 \times 10^9$ cfu/g
    *Bacillus subtilis* at $4.75 \times 10^9$ cfu/g
    *Pseudonomas putida* at $2.45 \times 10^8$ cfu/g
Carrier: Maltodextrin and Amino Acid Complex Referring now to the drawings and particularly to FIG. 4 thereof, there is shown diagrammatically a drip irrigation system 10 for maintaining regulated moisture content of the soil 11 in the root zone of plants under cultivation. The irrigation system 10 includes a control center 12 at which water from a supply is connected via appropriate control valves and pressure gauges (not shown) to a distribution network including a lateral 13. A microbe or bacterial solution 22 may be mixed with the irrigation water at the control center 12. In addition to the microbe or bacterial solution 22, additional fertilizer components can be used to increase crop yield.

Figure 4:
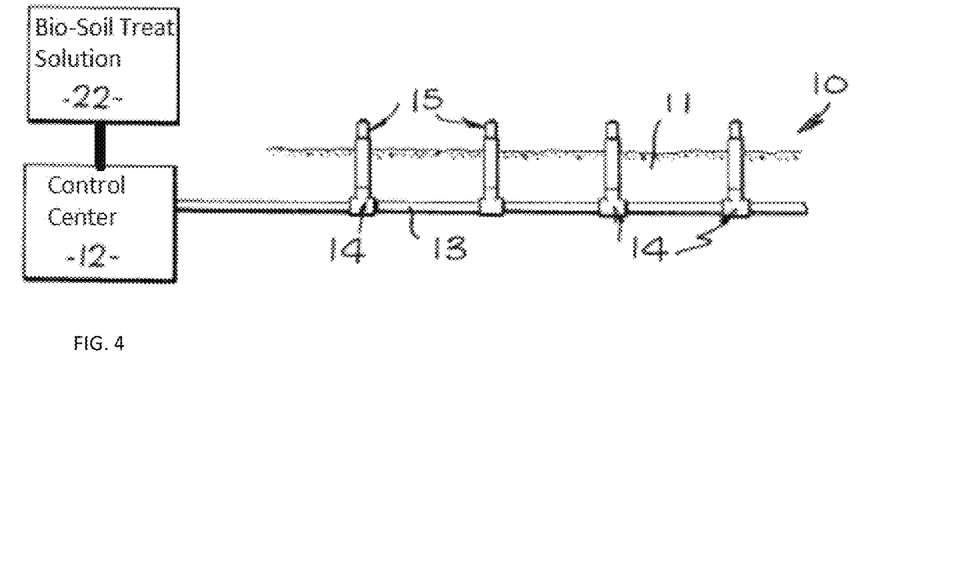
FIG. 4 is a simplified, diagrammatic view of a self-cleaning drip irrigation system using a bacterial composition.

The lateral 13 typically is underground, and provided with a plurality of T-connects 14 each of which conducts the supplied irrigation water upward above ground level to a drip irrigation nozzle 15 of the type disclosed herein. Each nozzle 15 functions to dispense the irrigation fluid at a slow but constant rate, independent of the fluid pressure present at the particular T-connect 14 associated with that nozzle. Uniform, regulated soil moisture content is achieved.

Drip and subsurface drip irrigation is used almost exclusively when using recycled municipal waste water. Regulations typically do not permit spraying water through the air that has not been fully treated to potable water standards.

Figure 5:
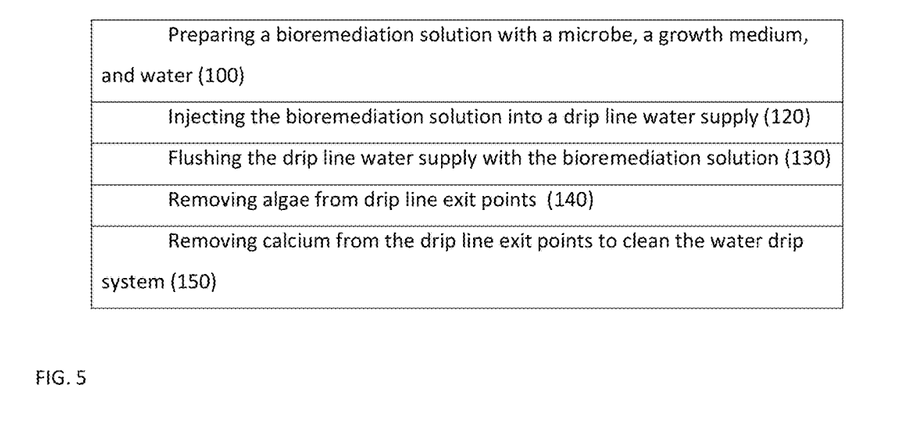
FIG. 5 shows an exemplary process of making the bacterial composition for bioremediation of drip line irrigation systems from clog and maintenance.

FIG. 5 shows an exemplary process of making the bacterial composition for bioremediation of drip line irrigation systems from clog and maintenance. In one embodiment, the solution 22 includes one or more microbes such as *Bacillus Subtilus, Bacilus amyloliquefaciens, Bacilus pumilus, Bacilus licheniformis*. The microbes are mixed in water with a carbon source such as sugar, molasses, or maltrodextrin. The microbes create an enzyme once it been incubated with water and carbon source, and the enzyme can be amylase or proteases, among others. In one embodiment, the process of FIG. 5 includes:

Preparing a bioremediation solution with a microbe, a growth medium, and water (100)
Injecting the bioremediation solution into a drip line water supply (120)
Flushing the drip line water supply with the bioremediation solution (130)
Removing algae from drip line exit points (140)
Removing calcium from drip line exit points to clean the water drip system (150)

The microbes (bacteria) are incubate with carbon source (such as sugar, molasses, or maltodextrin) along with water. It is then aerate for about 24 hours in one embodiment, and between 12-48 hours in other embodiments. This liquid is then injected through the drip line. In one embodiment, the solution 22 can have 1 part microbes, 10 part carbon source, and 1000 parts water.

*Bacillus* is a genus of gram-positive, rod-shaped bacteria and a member of the phylum Firmicutes. *Bacillus* species can be obligate aerobes (oxygen reliant), or facultative anaerobes (having the ability to be aerobic or anaerobic). They will test positive for the enzyme catalase when there has been oxygen used or present. Ubiquitous in nature, *Bacillus* includes both free-living (nonparasitic) and parasitic pathogenic species. Under stressful environmental conditions, the bacteria can produce oval endospores that are not true 'spores', but to which the bacteria can reduce themselves and remain in a dormant state for very long periods. These characteristics originally defined the genus, but not all such species are closely related, and many have been moved to other genera of the Firmicutes. Many species of *Bacillus* can produce copious amounts of enzymes which are made use of in different industries. Some species can form intracellular inclusions of polyhydroxyalkanoates under certain adverse environmental conditions, as in a lack of elements such as phosphorus, nitrogen, or oxygen combined with an excessive supply of carbon sources. Many *Bacillus* species are able to secrete large quantities of enzymes. *Bacillus amyloliquefaciens* is the source of a natural antibiotic protein barnase (a ribonuclease), alpha amylase used in starch hydrolysis, the protease subtilisin used with detergents, and the BamH1 restriction enzyme used in DNA research.

*Bacillus (B.) subtilis* is a Gram-positive bacterium, rod-shaped and catalase-positive. *B. subtilis* cells are typically rod-shaped, and are about 4-10 micrometers (μm) long and 0.25-1.0 μm in diameter, with a cell volume of about 4.6 fL at stationary phase. As with other members of the genus *Bacillus*, it can form an endospore, to survive extreme environmental conditions of temperature and desiccation. *B. subtilis* is heavily flagellated, which gives it the ability to move quickly in liquids. *B. subtilis* has proven highly amenable to genetic manipulation, and has become widely adopted as a model organism for laboratory studies, especially of sporulation, which is a simplified example of cellular differentiation. In terms of popularity as a laboratory model organism, *B. subtilis* is often considered as the Gram-positive equivalent of *Escherichia coli*, an extensively studied Gram-negative bacterium. This species is commonly found in the upper layers of the soil. Other members of the *Bacillus* species can be used, including:
    *Bacillus (B.) acidiceler*
    *B. acidicola*
    *B. acidiproducens*
    *B. acidoca Ida rius*

*B. acidoterrestris*
*B. aeolius*
*B. aerius*
*B. aerophilus*
*B. agaradhaerens*
*B. agri*
*B. aidingensis*
*B. akibai*
*B. alcalophilus*
*B. algicola*
*B. alginolyticus*
*B. alkalidiazotrophicus*
*B. alkalinitrilicus*
*B. alkalisediminis*
*B. alkalitelluris*
*B. altitudinis*
*B. alveayuensis*
*B. alvei*
*B. amyloliquefaciens*
*B. a.* subsp. *amyloliquefaciens*
*B. a.* subsp. *plantarum*
*B. amylolyticus*
*B. andreesenii*
*B. aneurinilyticus*
*B. anthracia*
*B. aquimaris*
*B. arenosi*
*B. arseniciselenatis*
*B. arsenicus*
*B. aurantiacus*
*B. arvi*
*B. aryabhattai*
*B. asahii*
*B. atrophaeus*
*B. axarquiensis*
*B. azotofixans*
*B. azotoformans*
*B. badius*
*B. barbaricus*
*B. bataviensis*
*B. beijingensis*
*B. benzoevorans*
*B. beringensis*
*B. berkeleyi*
*B. beveridgei*
*B. bogoriensis*
*B. boroniphilus*
*B. borstelensis*
*B. brevis Migula*
*B. butanolivorans*
*B. canaveralius*
*B. carboniphilus*
*B. cecembensis*
*B. cellulosilyticus*
*B. centrosporus*
*B. cereus*
*B. chagannorensis*
*B. chitinolyticus*
*B. chondroitinus*
*B. choshinensis*
*B. chungangensis*
*B. cibi*
*B. circulans*
*B. clarkii*
*B. clausii*
*B. coagulans*
*B. coahuilensis*

*B. cohnii*
*B. cornposti*
*B. curdlanolyticus*
*B. cycloheptanicus*
*B. cytotoxicus*
*B. daliensis*
*B. decisifrondis*
*B. decolorationis*
*B. deserti*
*B. dipsosauri*
*B. drentensis*
*B. edaphicus*
*B. ehimensis*
*B. eiseniae*
*B. enclensis*
*B. endophyticus*
*B. endoradicis*
*B. farraginis*
*B. fastidiosus*
*B. fengqiuensis*
*B. firmus*
*B. flexus*
*B. foraminis*
*B. fordii*
*B. formosus*
*B. fortis*
*B. fumarioli*
*B. funiculus*
*B. fusiformis*
*B. galactophilus*
*B. galactosidilyticus*
*B. galliciensis*
*B. gelatini*
*B. gibsonii*
*B. ginsengi*
*B. ginsengihumi*
*B. ginsengisoli*
*B. globisporus*
*B. g.* subsp. *globisporus*
*B. g.* subsp. *marinus*
*B. glucanolyticus*
*B. gordonae*
*B. gottheilii*
*B. graminis*
*B. halmapalus*
*B. haloalkaliphilus*
*B. halochares*
*B. halodenitrificans*
*B. halodurans*
*B. halophilus*
*B. halosaccharovorans*
*B. hemicellulosilyticus*
*B. hemicentroti*
*B. herbersteinensis*
*B. horikoshii*
*B. horneckiae*
*B. horti*
*B. huizhouensis*
*B. humi*
*B. hwajinpoensis*
*B. idriensis*
*B. indicus*
*B. infantis*
*B. infernus*
*B. insolitus*
*B. invictae*
*B. iranensis*

B. isabeliae
B. isronensis
B. jeotgali
B. kaustophilus
B. kobensis
B. kochii
B. kokeshiiformis
B. koreensis
B. korlensis
B. kribbensis
B. krulwichiae
B. laevolacticus
B. larvae
B. laterosporus
B. lautus
B. lehensis
B. lentimorbus
B. lentus
B. licheniformis
B. ligniniphilus
B. litoralis
B. locisalis
B. luciferensis
B. luteolus
B. luteus
B. macauensis
B. macerans
B. macquariensis
B. macyae
B. malacitensis
B. mannanilyticus
B. marisflavi
B. marismortui
B. marmarensis
B. massiliensis
B. megaterium
B. mesonae
B. methanolicus
B. methylotrophicus
B. migulanus
B. mojavensis
B. mucilaginosus
B. muralis
B. murimartini
B. mycoides
B. naganoensis
B. nanhaiensis
B. nanhaiisediminis
B. nealsonii
B. neidei
B. neizhouensis
B. niabensis
B. niacini
B. novalis
B. oceanisediminis
B. odysseyi
B. okhensis
B. okuhidensis
B. oleronius
B. oryzaecorticis
B. oshimensis
B. pabuli
B. pakistanensis
B. pallidus
B. pallidus
B. panacisoli
B. panaciterrae B. pantothenticus
B. parabrevis
B. paraflexus
B. pasteurii
B. patagoniensis
B. peoriae
B. persepolensis
B. persicus
B. pervagus
B. plakortidis
B. pocheonensis
B. polygoni
B. polymyxa
B. popilliae
B. pseudalcalophilus
B. pseudofirmus
B. pseudomycoides
B. psychrodurans
B. psychrophilus
B. psychrosaccharolyticus
B. psychrotolerans
B. pulvifaciens
B. pumilus
B. purgationiresistens
B. pycnus
B. qingdaonensis
B. qingshengii
B. reuszeri
B. rhizosphaerae
B. rigui
B. ruris
B. safensis
B. salarius
B. salexigens
B. saliphilus
B. schlegelii
B. sediminis
B. selenatarsenatis
B. selenitireducens
B. seohaeanensis
B. shacheensis
B. shackletonii
B. siamensis
B. silvestris
B. simplex
B. siralis
B. smithii
B. soli
B. solimangrovi
B. solisalsi
B. songklensis
B. sonorensis
B. sphaericus
B. sporothermodurans
B. stearothermophilus
B. stratosphericus
B. subterraneus
B. subtilis
B. s. subsp. inaquosorum
B. s. subsp. spizizenii
B. s. subsp. subtilis
B. taeanensis
B. tequilensis
B. thermantarcticus
B. thermoaerophilus
B. thermoamylovorans
B. thermocatenulatus B. *thermocloacae*
B. *thermocopriae*
B. *thermodenitrificans*
B. *thermoglucosidasius*
B. *thermolactis*
B. *thermoleovorans*
B. *thermophilus*
B. *thermoruber*
B. *thermosphaericus*
B. *thiaminolyticus*
B. *thioparans*
B. *thuringiensis*
B. *tianshenii*
B. *trypoxylicola*
B. *tusciae*
B. *validus*
B. *vallismortis*
B. *vedderi*
B. *velezensis*
B. *vietnamensis*
B. *vireti*
B. *vulcani*
B. *wakoensis*
B. *weihenstephanensis*
B. *xiamenensis*
B. *xiaoxiensis*
B. *zhanjiangensis*

Figure 6:
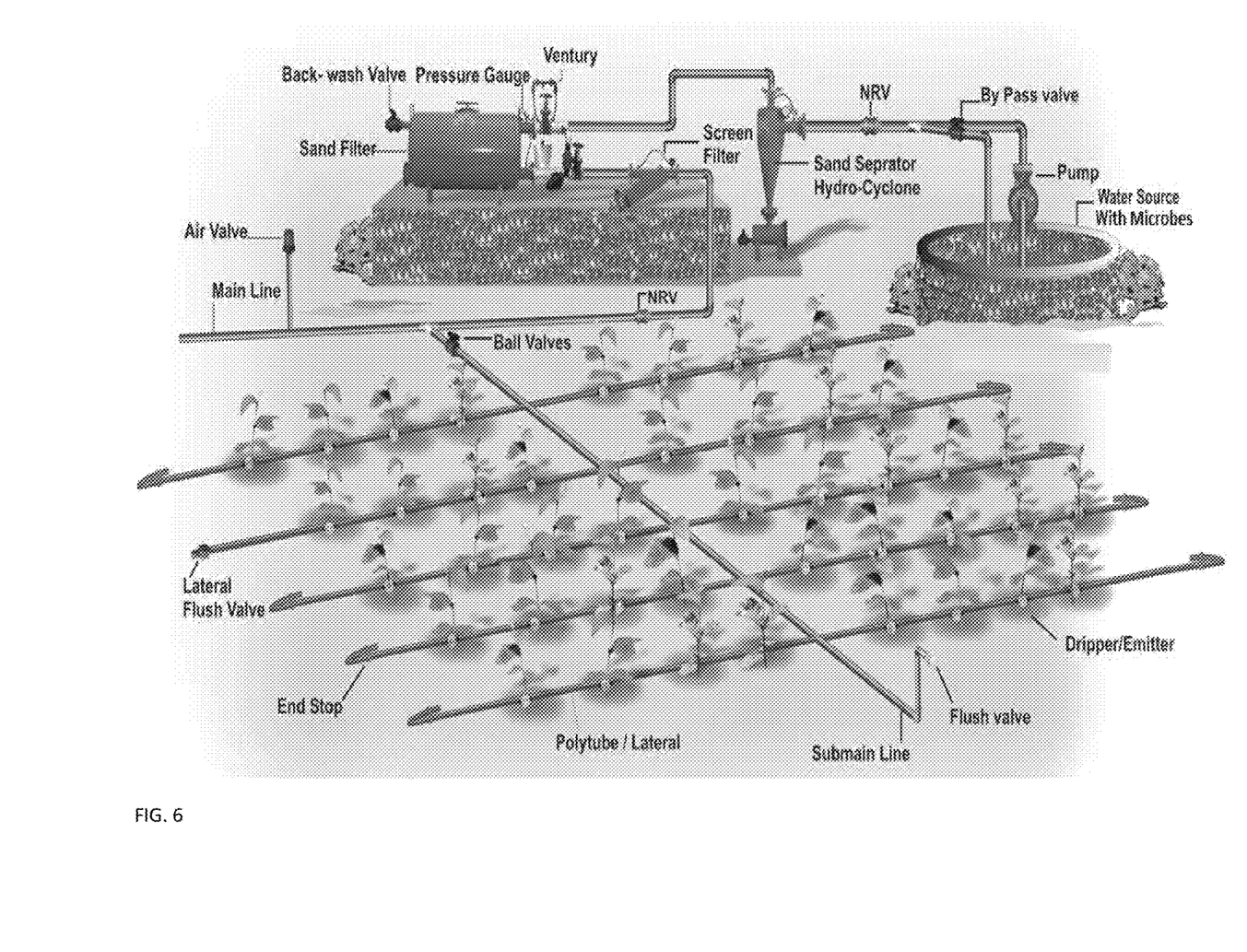
FIG. 6 is a simplified, diagrammatic view of a large scale self-cleaning drip irrigation system that uses the bioremediation composition of FIG. 1.

FIG. 6 shows another exemplary self-cleaning drip irrigation using microbes. Components used in drip irrigation (listed from the water source) include:

Pump or pressurized water source with microbes mixed therein
Water filter(s) or filtration systems: sand separator, Fertigation systems (Venturi injector) and chemigation equipment (optional)
- Backwash controller (Backflow prevention device)
- Pressure Control Valve (pressure regulator)
- Main line (larger diameter pipe and pipe fittings)
- Hand-operated, electronic, or hydraulic control valves and safety valves
- Smaller diameter polytube (often referred to as "laterals")
- Poly fittings and accessories (to make connections)
- Emitting devices at plants (emitter or dripper, micro spray head, inline dripper or inline driptube)
- In drip irrigation systems, pump and valves may be manually or automatically operated by a controller.

In one embodiment, an apparatus for cleaning a water drip system includes an irrigation water source; a bio-remediation container housing a solution with microbes, a growth medium, and water; and a delivery device for injecting the bioremediation solution into a water supply and flushing the water supply with the bioremediation solution, wherein the solution removes algae, calcium, or both from drip line exit points to clean the water drip system.

In implementations, the container aerates the solution for a predetermined period and then injecting the solution through a drip line. The drip system provides pulsed irrigation.Emitters placed at a predetermined distance and flow per hour as per crop distance. A liquid fertilizer mixed with the irrigation water.

While the microbes perform the self cleaning, large drip irrigation systems can additionally employ some type of filter to prevent clogging of the small emitter flow path by small waterborne particles. New technologies are now being offered that minimize clogging. Some residential systems are installed without additional filters since potable water is already filtered at the water treatment plant. Last line filters just before the final delivery pipe can additionally be used in addition to any other filtration system due to fine particle settlement and accidental insertion of particles in the intermediate lines.

Because of the way the water is applied in a drip system, traditional surface applications of timed-release fertilizer are sometimes ineffective, so drip systems can mix liquid fertilizer with the irrigation water. This is called fertigation; fertigation and chemigation (application of pesticides and other chemicals to periodically clean out the system, such as chlorine or sulfuric acid) use chemical injectors such as diaphragm pumps, piston pumps, or aspirators. The chemicals may be added constantly whenever the system is irrigating or at intervals. Fertilizer savings of up to 95% are being reported from recent university field tests using drip fertigation and slow water delivery as compared to timed-release and irrigation by micro spray heads.

The drip irrigation may help achieve water conservation by reducing evaporation and deep drainage when compared to other types of irrigation such as flood or overhead sprinklers since water can be more precisely applied to the plant roots. In addition, drip can eliminate many diseases that are spread through water contact with the foliage. Finally, in regions where water supplies are severely limited, there may be no actual water savings, but rather simply an increase in production while using the same amount of water as before. In very arid regions or on sandy soils, the preferred method is to apply the irrigation water as slowly as possible.

Pulsed irrigation is sometimes used to decrease the amount of water delivered to the plant at any one time, thus reducing runoff or deep percolation. Pulsed systems are typically expensive and require extensive maintenance. Therefore, the latest efforts by emitter manufacturers are focused toward developing new technologies that deliver irrigation water at ultra-low flow rates, i.e. less than 1.0 liter per hour. Slow and even delivery further improves water use efficiency without incurring the expense and complexity of pulsed delivery equipment.

An emitting pipe is a type of drip irrigation tubing with emitters pre-installed at the factory with specific distance and flow per hour as per crop distance.

An emitter restricts water flow passage through it, thus creating head loss required (to the extent of atmospheric pressure) in order to emit water in the form of droplets. This head loss is achieved by friction / turbulence within the emitter.

While the present invention has been described in terms of a carpet cleaning solution and rotary scrubbing machines, one skilled in the art will realize that the structure and techniques of the present invention can be applied to many appliances. The present invention may be applied in any situation where cleaning is required.

The above description is for the purpose of illustrating and not limiting the present invention, and teaching the person of ordinary skill in the art how to practice the invention. It is not intended to detail all those obvious modifications and variations of it which will become apparent to the skilled worker upon reading the description. It is intended, however, that all such obvious modifications and variations be included within the scope of the present invention as defined in the appended claims. The claims are meant to cover the claimed components and steps in any sequence which is effective to meet the objectives there intended, unless the context specifically indicates the contrary.

The patents, papers, and book excerpts cited above are hereby incorporated herein by reference in in their entireties.

What is claimed is:

1. A method for cleaning a water drip system, comprising:

preparing a bioremediation solution with microbes, a growth medium, and water;

iteratively and selectively breeding generations of microbes for microbial strain selection with predetermined microbial gene profiles to arrive at a predetermined microbial solution in a highly concentrated form of at least $1\times10^9$ cfu/ml (colony-forming units per milliliter), wherein multiple single microbial series are separately cultivated and followed with cross cultivation among the microbial series in a specific sequence, and by-products produced by the crossly cultivated microbial series are provided as a highly concentrated solution to digest excess nutrients clogging the drip system;

injecting the bioremediation solution into a water supply; and flushing the water drip system with the bioremediation solution, wherein the microbes remove algae from the water drip system.

2. The method of claim 1, comprising selecting a member of *Bacillus* as the microbe.

3. The method of claim 1, comprising:

removing algae from drip line exit points during flushing; and removing calcium from the drip line exit points during flushing to clean the water drip system.

4. The method of claim 1, wherein the growth medium comprises a carbon source, sugar, molasses, or maltodextrin.

5. The method of claim 1, comprising mixing the solution with 1part microbes, 10 part carbon source, and 1000 parts water.

6. The method of claim 1, comprising aerating the solution for at least six hours and then injecting the solution through a drip line.

7. The method of claim 1, comprising performing pulsed irrigation.

8. The method of claim 1, wherein the drip system includes liquid emitters, further comprising cleaning emitters at a predetermined distance and flow per hour as per crop distance.

9. The method of claim 1, wherein the bioremediation solution is a highly concentrated form of at least $1\times10^9$ cfu/ml.

10. The method of claim 1, comprising selecting the microbe from *Bacillus* (*B*.) *acidiceler,B. acidicola, B. acidiproducens, B. acidocaldarius, B. acidoterrestrisr, B. aeolius, B. aerius, B. aerophilus, B. agaradhaerens, B. agri, B. aidingensis, B. akibai, B. alcalophilus, B. algicola, B. alginolyticus, B. alkalidiazotrophicus, B. alkalinitrilicus, B. alkalisediminis, B. alkalitelluris, B. altitudinis, B. alveayuensis, B. alvei, B. amyloliquefaciens, B. a*. subsp. *amyloliquefaciens, B. a*. subsp. *plantarum, B. mylolyticus, B. andreesenii, B. aneurinilyticus, B. anthracia, B. aquimaris, B. arenosi, B. arseniciselenatis, B. arsenicus, B. aurantiacus, B. arvi, B. aryabhattai, B. asahii, B. atrophaeus, B. axarquiensis, B. azotofixans, B. azotoformans, B. badius, B. barbaricus, B. bataviensis, B. beijingensis, B. benzoevorans, B. beringensis, B. berkeleyi, B. beveridgei, B. bogoriensis, B. boroniphilus, B. borstelensis, B. brevis Migula, B. butanolivorans, B. canaveralius, B. carboniphilus, B. cecembensis, B. cellulosilyticus, B. centrosporus, B. cereus, B. chagannorensis, B. chitinolyticus, B. chondroitinus, B. choshinensis, B. chungangensis, B. cibi, B. circulans, B. clarkii, B. clausii, B. coagulans, B. coahuilensis, B. cohnii, B. composti, B. curdlanolyticus, B. cycloheptanicus, B. cytotoxicus, B. daliensis, B. decisifrondis, B. decolorationis, B. deserti, B. dipsosauri, B. drentensis, B. edaphicus, B. ehimensis, B. eiseniae, B. enclensis, B. endophyticus, B. endoradicis, B. farraginis, B. fastidiosus, B. fengqiuensis, B. firmus, B. flexus, B. foraminis, B. fordii, B. formosus, B. fortis, B. fumarioli, B. funiculus, B. fusiformis, B. galactophilus, B. galactosidilyticus, B. galliciensis, B. gelatini, B. gibsonii, B. ginsengi, B. ginsengihumi, B. ginsengisoli, B. globisporus, B. g*. subsp. *globisporus, B. g*. subsp. *marinus, B. glucanolyticus, B. gordonae, B. gottheilii, B. graminis, B. halmapalus, B. haloalkaliphilus, B. halochares, B. halodenitrificans, B. halodurans, B. halophilus, B. halosaccharovorans, B. hemicellulosilyticus, B. hemicentroti, B. herbersteinensis, B. horikoshii, B. horneckiae, B. horti, B. huizhouensis, B. humi, B. hwajinpoensis, B. idriensis, B. indicus, B. infantis, B. infernus, B. insolitus, B. invictae, B. iranensis, B. isabeliae, B. isronensis, B. jeotgali, B. kaustophilus, B. kobensis, B. kochii, B. kokeshiiformis, B. koreensis, B. korlensis, B. kribbensis, B. krulwichiae, B. laevolacticus, B. larvae, B. laterosporus, B. lautus, B. lehensis, B. lentimorbus, B. lentus, B. licheniformis, B. ligniniphilus, B. litoralis, B. locisalis, B. luciferensis, B. luteolus, B. luteus, B. macauensis, B. macerans, B. macquariensis, B. macyae, B. malacitensis, B. mannanilyticus, B. marisflavi, B. marismortui, B. marmarensis, B. massiliensis, B. megaterium, B. mesonae, B. methanolicus, B. methylotrophicus, B. migulanus, B. mojavensis, B. mucilaginosus, B. muralis, B. murimartini, B. mycoides, B. naganoensis, B. nanhaiensis, B. nanhaiisediminis, B. nealsonii, B. neidei, B. neizhouensis, B. niabensis, B. niacini, B. novalis, B. oceanisediminis, B. odysseyi, B. okhensis, B. okuhidensis, B. oleronius, B. oryzaecorticis, B. oshimensis, B. pabuli, B. pakistanensis, B. pallidus, B. pallidus, B. panacisoli, B. panaciterrae, B. pantothenticus, B. parabrevis, B. paraflexus, B. pasteurii, B. patagoniensis, B. peoriae, B. persepolensis, B. persicus, B. pervagus, B. plakortidis, B. pocheonensis, B. polygoni, B. polymyxa, B. popilliae, B. pseudalcalophilus, B. pseudofirmus, B. pseudomycoides, B. psychrodurans, B. psychrophilus, B. psychrosaccharolyticus, B. psychrotolerans, B. pulvifaciens, B. pumilus, B. purgationiresistens, B. pycnus, B. qingdaonensis, B. qingshengii, B. reuszeri, B. rhizosphaerae, B. rigui, B. ruris, B. safensis, B. salarius, B. salexigens, B. saliphilus, B. schlegelii, B. sediminis, B. selenatarsenatis, B. selenitireducens, B. seohaeanensis, B. shacheensis, B. shackletonii, B. siamensis, B. silvestris, B. simplex, B. siralis, B. smithii, B. soli, B. solimangrovi, B. solisalsi, B. songklensis, B. sonorensis, B. sphaericus, B. sporothermodurans, B. stearothermophilus, B. stratosphericus, B. subterraneus, B. subtilis, B. s*. subsp. *inaquosorum, B. s*. subsp. *spizizenii, B. s*. subsp. *subtilis, B. taeanensis, B. tequilensis, B. thermantarcticus, B. thermoaerophilus, B. thermoamylovorans, B. thermocatenulatus, B. thermocloacae, B. thermocopriae, B. thermodenitrificans, B. thermoglucosidasius, B. thermolactis, B. thermoleovorans, B. thermophilus, B. thermoruber, B. thermosphaericus, B. thiaminolyticus, B. thioparans, B. thuringiensis, B. tianshenii, B. trypoxylicola, B. tusciae, B. validus, B. vallismortis, B. vedderi, B. velezensis, B. vietnamensis, B. vireti, B. vulcani, B. wakoensis, B. weihenstephanensis, B. xiamenensis, B. xiaoxiensis, B. zhanjiangensis.*

11. The method of claim 1, comprising:

preparing a microbial solution with microbes, a growth medium, and water;

iteratively and selectively breeding generations of microbes to arrive at a predetermined microbial solution in a highly concentrated form of at least $1\times10^9$ cfu/ml (colony-forming units per milliliter).

12. The method of claim 11, comprising dispensing the microbial solution into the water, wherein the microbes metabolizes excess nutrients and uses microbial desalination to reduce water salinity.

13. The method of claim 1, comprising selecting a member of *Bacillus* as the microbe.

14. The method of claim 11, wherein the growth medium comprises a carbon source.

15. The method of claim 11, wherein the growth medium comprises sugar, molasses, or maltodextrin.

16. The method of claim 1, comprising mixing the solution with 1 part microbes, 10 part carbon source, and 1000 parts water.

* * * * *